US006974485B2

(12) United States Patent
Belcour-Castro et al.

(10) Patent No.: US 6,974,485 B2
(45) Date of Patent: Dec. 13, 2005

(54) **USE OF AN EXTRACT OF *MYRSINE AFRICANA* IN OXIDATION DYEING FOR DYEING KERATIN FIBRES**

(75) Inventors: Béatrice Belcour-Castro, Joinville le Pont (FR); Hervé Burgaud, Damartin en Goele (FR); Georges Hussler, Aulnay sous Bois (FR); Michel Seite, Paris (FR)

(73) Assignee: L'Oreal S.A. (FR)

( * ) Notice: Subject to any disclaimer, the term of this patent is extended or adjusted under 35 U.S.C. 154(b) by 252 days.

(21) Appl. No.: 10/293,481

(22) Filed: Nov. 14, 2002

(65) Prior Publication Data

US 2003/0115687 A1 Jun. 26, 2003

(30) Foreign Application Priority Data

Nov. 14, 2001 (FR) .......................................... 01 14719

(51) Int. Cl.$^7$ ................................................ A61K 7/13
(52) U.S. Cl. ....................... 8/405; 8/406; 8/408; 8/409; 8/410; 8/411; 8/421; 8/436; 8/463; 8/565; 8/567; 8/568; 8/573; 8/646; 544/224; 546/250
(58) Field of Search .......................... 8/405, 406, 408, 8/409, 410, 411, 421, 436, 463, 565, 567, 568, 573, 646; 544/224; 546/250

(56) References Cited

U.S. PATENT DOCUMENTS

| 4,003,699 A | * | 1/1977 | Rose et al. ..................... 8/409 |
| 4,823,985 A | | 4/1989 | Grollier et al. ................. 222/1 |
| 5,061,289 A | | 10/1991 | Clausen et al. ................ 8/405 |
| 5,380,340 A | | 1/1995 | Neunhoeffer et al. .......... 8/409 |
| 5,766,576 A | | 6/1998 | Löwe et al. .................. 424/62 |
| 6,099,592 A | | 8/2000 | Vidal et al. ..................... 8/409 |
| 6,099,593 A | | 8/2000 | Terranova et al. ............. 8/409 |
| 6,837,908 B2 | | 1/2005 | Vidal et al. ..................... 8/405 |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 770 375 | 5/1997 |
| EP | 0 776 652 | 6/1997 |
| FR | 2 586 913 | 3/1987 |
| FR | 2731162 | 9/1996 |
| FR | 2 733 749 | 11/1996 |
| FR | 2 750 048 | 12/1997 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |

OTHER PUBLICATIONS

T. Johns et al., "Saponins and phenolic content in plant dietary additives of a traditional subsistence community, the Batemi of Ngorongoro District, Tanzania," Journal of Ethnopharmacology, Elsevier Scientific Publishers Ltd., IE, vol. 66, Jul. 1999, pp. 1–10.

W.H.O. Ernst et al., "Seasonal variation in phenolics in several savanna tree species in Botswana," ACTA Bot. Neerl., vol. 40, No. 1, 1991, pp. 67–74.

English language Derwent Abstract of EP 0 770 375, May 2, 1997.

English language Derwent Abstract of EP 0 776 652, Jun. 4, 1997.

English language Derwent Abstract of JP 2–19576, Jan. 23, 1990.

English language Derwent Abstract of JP 5–163124, Jun. 29, 1993.

* cited by examiner

*Primary Examiner*—Mark Kopec
*Assistant Examiner*—Eisa Elhilo
(74) *Attorney, Agent, or Firm*—Finnegan, Henderson, Farabow, Garrett & Dunner LLP

(57) ABSTRACT

Use of an extract of the plant *Myrsine africana* in oxidation dyeing for dyeing keratin fibres, a novel composition comprising this plant extract, a process for the oxidation dyeing of keratin fibres using this composition, as well as the coloured products obtained using the composition.

27 Claims, No Drawings

USE OF AN EXTRACT OF *MYRSINE AFRICANA* IN OXIDATION DYEING FOR DYEING KERATIN FIBRES

Disclosed herein are the use of an extract of *Myrsine africana* in oxidation dyeing of keratin fibres, a novel composition comprising this plant extract, and a process for the oxidation dyeing of keratin fibres using this composition.

It is a well-known practice to dye keratin fibres, such as human hair, with dye compositions comprising oxidation dye precursors, generally known as oxidation bases chosen, for example, from ortho- and para-phenylenediamines, ortho- and para-aminophenols and heterocyclic compounds. These oxidation bases are colourless or weakly coloured compounds which, when combined with oxidizing products, may give rise to coloured compounds by a process of oxidative condensation.

It is also well-known that the shades obtained with these oxidation bases may be varied by combining them with couplers or coloration modifiers. The couplers or coloration modifiers can be chosen, for example, from aromatic meta-diamines, meta-aminophenols, meta-diphenols and certain heterocyclic compounds, such as indole compounds.

The variety of molecules that may be used as oxidation bases and couplers allows a wide range of colours to be obtained.

The "permanent" coloration obtained by means of these oxidation dyes should satisfy a certain number of requirements. It should be free of toxicological drawbacks, it should allow shades to be obtained in the desired intensity, and it should show good resistance to external agents, such as light, bad weather, washing, permanent-waving, perspiration and rubbing.

The colorants should also be able to cover grey hair. They should be as unselective as possible, i.e., they should allow the smallest possible differences in coloration along the same length of keratin fibre, which may be differently sensitized (i.e., damaged) from its end to its root.

There is a constant need to develop compositions, such as those derived from natural substances, that show no substantial aggressive behaviour towards keratin fibres.

For example, European patent application EP 776 652 describes the use of a plant extract in oxidation dyeing for dyeing keratin fibres. The plant extracts disclosed in the patent application are protein hydrolysates.

The present disclosure relates to novel compositions from plant extracts for dyeing keratin fibres by oxidation dyeing. These compositions may respect the nature of the keratin fibres and may give powerful, relatively unselective and resistant dyeing results. These compositions may be capable of giving rise to novel powerful dyes that can give varied shades.

This disclosure relates to the use of an extract of *Myrsine africana* as a dye precursor for dyeing keratin fibres by oxidation dyeing.

The term "dye precursor" refers to an uncoloured compound which, under certain conditions, may be converted into a coloured product.

In one embodiment, a composition is disclosed for dyeing keratin fibres by oxidation dyeing, comprising, in a medium that is suitable for dyeing keratin fibres, at least one extract of *Myrsine africana* and at least one compound chosen from compounds of the formula (I) and cosmetically acceptable acid and base addition salts thereof:

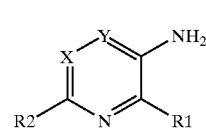

wherein $R_1$ is chosen from radicals of $NR_4R_5$, wherein $R_4$ and $R_5$, which may be identical or different, are chosen from a hydrogen atom, alkyl radicals optionally substituted with at least one radical chosen from hydroxyl, alkoxy, carboxyl, amino, monoalkylamino and dialkylamino radicals in which the alkyl radical is also optionally substituted with at least one radical chosen from hydroxyl, alkoxy, carboxyl, amino, monoalkylamino and dialkylamino radicals; or $R_4$ and $R_5$ may form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, such as $C_1$–$C_2$ monoalkylamino and dialkylamino radicals; the heterocycle optionally comprising at least one other hetero atom chosen from O, S, $SO_2$ and NR", wherein R" is chosen from a hydrogen atom and $C_1$–$C_4$ alkyl radicals, $R_2$ is chosen from radicals of $NR_6R_7$, wherein $R_6$ and $R_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_6$ and $R_7$ may form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, such as $C_1$–$C_2$ monoalkylamino and dialkylamino radicals; the heterocycle optionally comprising at least one other hetero atom chosen from O, S, $SO_2$ and NR", wherein R" is chosen from a hydrogen atom and $C_1$–$C_4$ alkyl radicals, and X—Y is chosen from RC—CR' and N—CR, wherein R and R' are chosen from a hydrogen atom, alkyl radicals, a hydroxyl radical and amino radicals.

Unexpectedly and surprisingly, it has been discovered that a composition comprising at least one extract of *Myrsine africana* and optionally at least one compound chosen from compounds of formula (I) and salts thereof as set forth above, can be used for the oxidation dyeing of keratin fibres, such as human hair. The use of such a composition may result, for example, in novel shades.

As used herein, the term "alkyl" means a radical chosen from saturated, linear and branched radicals comprising, except where otherwise mentioned, from 1 to 10 carbon atoms, such as from 1 to 6 carbon atoms and wherein the radicals may be optionally substituted. The term "alkoxy" means alkyl-O, wherein the term "alkyl" has the definition given above. The term "amino" means the —NH$_2$ radical. The term "monoalkylamino" or "dialkylamino" respectively means an amino radical, wherein one or two of the hydrogen atoms are replaced with an alkyl radical as defined above.

The heterocycles may be chosen, for example, from pyrrolidine, piperidine, homopiperidine, piperazine, homopiperazine and diazepane rings. As used herein, heterocycles do not contain a peroxide bond or diazo or nitroso radicals.

The at least one compound chosen from compounds of formula (I) may be chosen, for example, from 2,3-diamino-6-(1-pyrrolidinyl)pyridine, 2,3-diamino-6-(4-hydroxy-1-pyrrolidinyl)pyridine, 2-(1-pyrrolidinyl)-3-amino-6-(1-pyrrolidinyl)pyridine, 2,4,5,6-tetraamino-pyrimidine, 4-hydroxy-2,5,6-triaminopyrimidine and 2,5,6-triaminopyrimidine.

In one embodiment, the at least one compound chosen from compounds of formula (I) may be chosen, for example, from compounds of the formula (Ia):

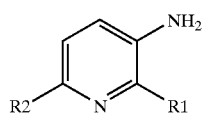

(Ia)

wherein $R_1$ and $R_2$ are as defined above.

In another embodiment, $R_1$ is chosen from radicals of $NR_4R_5$, wherein $R_4$ and $R_5$, which may be identical or different, are chosen from a hydrogen atom, alkyl radicals, and hydroxyalkyl radicals, or $R_4$ and $R_5$, together with the nitrogen atom to which they are attached, form a 5- to 7-membered ring; $R_2$ is chosen from radicals of $NR_6R_7$, wherein $R_6$ and $R_7$, which may be identical or different, are chosen from a hydrogen atom, alkyl and hydroxyalkyl radicals, or $R_6$ and $R_7$, together with the nitrogen atom to which they are attached, form a 5- to 7-membered ring.

For example, $R_4$ and $R_5$ or $R_6$ and $R_7$, together with the nitrogen atom to which they are attached, may form 2,5-dimethylpyrrolidine, proline, 3-hydroxyproline, 4-hydroxyproline, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxy-pyrrolidine, 3,4-dihydroxypyrrolidine, 3-amino-pyrrolidine, 3-methylaminopyrrolidine, 4-amino-3-hydroxypyrrolidine, 3-hydroxy-4-(2-hydroxyethyl)-aminopyrrolidine, 2,6-dimethylpiperidine, 2-carboxy-piperidine, 2-carboxamidopiperidine, 2-hydroxymethyl-piperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, diazepam, N-methyldiazepam and N-(2-hydroxyethyl)diazepam.

$R_4$ and $R_5$ may, for example, be a hydrogen atom or, together with the nitrogen atom to which they are attached, form a pyrrolidine ring. $R_6$ and $R_7$, together with the nitrogen atom to which they are attached, may form, for example, a 1-pyrrolidinyl ring, which may be optionally substituted.

In another embodiment, the at least one compound chosen from compounds of formula (I) may be chosen, for example, from compounds of the following formulae (Ia1) and (Ia2):

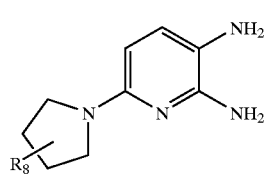

(Ia1)

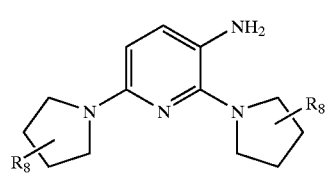

(Ia2)

wherein $R_8$ is chosen from a hydrogen atom, halogen atoms, hydroxyl, alkoxy, carboxyl, amino, carboxamido, sulphonamido, monoalkylamino and dialkylamino radicals and $C_1$–$C_6$ alkyl radicals optionally substituted with at least one radical chosen from hydroxyl, amino, carboxyl, monoalkylamino and dialkylamino radicals, such as $C_1$–$C_2$ monoalkylamino and dialkylamino radicals.

The at least one compound chosen from compounds of formula (I) may be chosen, for example, from 2,3-diamino-6-(1-pyrrolidinyl)pyridine, 2,3-diamino-6-(4-hydroxy-1-pyrrolidinyl)pyridine and 2-(1-pyrrolidinyl)-3-amino-6-(1-pyrrolidinyl)pyridine.

In another embodiment, the at least one compound chosen from compounds of formula (I) may be chosen, for example, from compounds of formula (Ib):

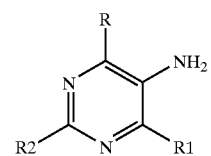

(Ib)

wherein $R_1$, $R_2$ and R are as defined above.

For example, R is chosen, for example, from amino and hydroxyl radicals. For example, R, $R_1$ and $R_2$ are each $NH_2$.

*Myrsine africana* is a plant of the Myrsinacea family, having the common name Cape myrtle or African boxwood, and may be found in Africa, Western China, and the Himalayas. It can be a very slow-growing shrub with perennial leaves and monoecious flowers, the fruit of which has a single seed.

The extract of *Myrsine africana* may be obtained, for example, according to standard techniques for extracting plants. For example, any extraction method known to a person of ordinary skill in the art may be used to prepare this extract. Mention may be made, for example, of alcoholic extracts, such as ethanolic or aqueous-alcoholic extracts.

Such techniques are described, for example, in "Methods in Plant Biochemistry", vol. 1, 1989, by Dey and Harborne, Academic Press edition. These extracts may be obtained, for example, from the whole plant, wherein the plant may be at various stages of physiological maturity. Cell strains derived from the plant may, for example, also be used. The cell strains may be obtained, for example, according to techniques described in "Plant tissue culture: theory and practice"—1953, Bhojwani and Razdan, published by Elsevier, or "La culture des tissus végétaux [Plant tissue culture]"—1959, Gautheret, published by Masson.

It may be possible, for example, to use an extract of *Myrsine africana* prepared by the method described in French Patent Application No. 95/02379. According to this method, for example, (i) the plant material is first ground in an aqueous solution under cold conditions; (ii) the particles in suspension are then removed from the aqueous solution obtained previously; (iii) the aqueous solution thus obtained is sterilized. This aqueous solution corresponds to the extract.

The grinding procedure (i) may, for example, be replaced with an operation of simple freezing of the plant tissues (for example, at about −20° C.), followed by an aqueous extraction repeating (ii) and (iii) described above. The product of this aqueous extraction may also be, for example, freeze-dried to obtain a solids content (depending on the nature of the initial source, the solids content ranging, for example, from about 5 to about 70 g may be found per litre of the aqueous extract).

In another embodiment, the plant extract is an aqueous extract obtained from the aerial parts (e.g., stems and leaves) of the *Myrsine africana* plant.

The extract of *Myrsine africana* comprises, for example, 3-(β-D-glucopyranosyloxy)-4,5-dihydroxy-toluene, which is a compound of formula (II) below. Disclosed herein is a compound of the formula (II), which may be obtained, for example, from an extract of *Myrsine africana*:

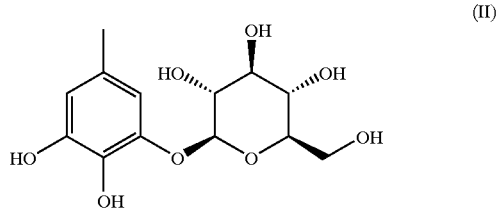

(II)

According to another embodiment and further disclosed herein is a composition for the oxidation dyeing of keratin fibres, comprising, in a medium that is suitable for dyeing keratin fibres, at least one dye precursor of the formula (I) as defined above and 3-(β-D-glucopyranosyloxy)-4,5-dihydroxytoluene, which may be obtained from an aqueous extract of *Myrsine africana*.

On oxidizing the composition, a coloured product may be formed in the medium resulting, for example, from the oxidative condensation of a compound of the formula (I) with a compound of the formula (II). For example, starting with a composition comprising 3-(β-D-glucopyranosyloxy)-4,5-dihydroxytoluene and a compound of the formula (Ia1) below:

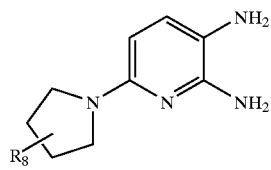

at least one of the coloured products of the formulae (IIIa), (IIIb) and (IIIc) described below may be formed:

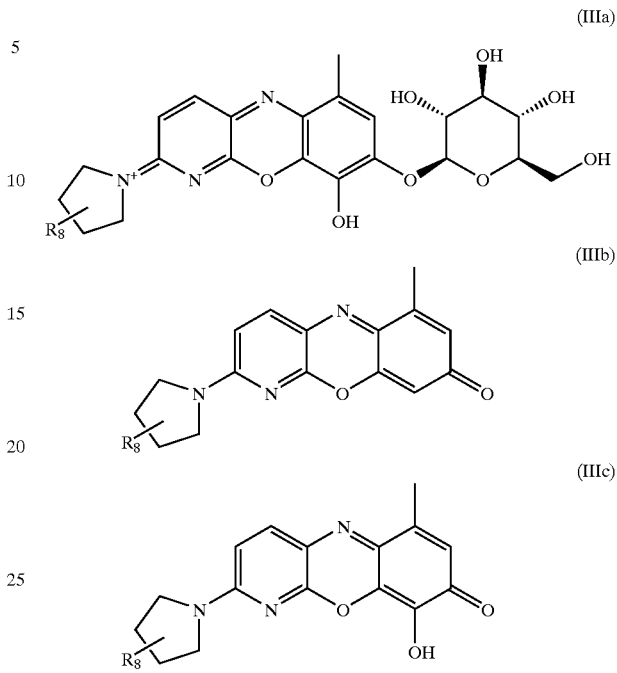

wherein $R_8$ is defined the same as above.

These three coloured products may result from an oxidative coupling of the diaminopyridine compound and of the glucosyl derivative of trihydroxytoluene. This coupling may be followed by a nucleophilic substitution of the amino group in position C-2 of the diaminopyridine compound with an OH group of the trihydroxytoluene derivative, this cyclization resulting in the loss of ammonia. Other coloured products may be obtained according to the same mechanism from the compounds of formula (I).

Further disclosed herein are those coloured products that may be obtained from the present composition. The coloured products may, for example, be in the form of pigments, and may be used, for example, as direct dyes for the direct dyeing of the hair, or may be incorporated, for example, into cosmetic products, such as makeup products.

Oxidative self-condensation of the at least one compound chosen from compounds of formula (I), such as compounds of the formulae (Ia1) and (Ia2), can be promoted in the presence of an extract of *Myrsine africana*. For example, the appearance of the colour may be faster in the presence of an extract of *Myrsine africana*.

In one embodiment, the extract of *Myrsine africana* may be present in an amount ranging from about 0.1% to about 10% by weight, for example, from about 0.5% to about 5% by weight, relative to the weight of the composition.

In another embodiment, the composition may further comprise at least one oxidation base chosen from oxidation bases that are conventionally used in oxidation dyeing, such as para-phenylenediamines, bis(phenyl)alkylenediamines, para-aminophenols, orthoaminophenols and heterocyclic bases, and the addition salts thereof.

The para-phenylenediamines may be chosen, for example, from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-diethyl-para-phenylenediamine, N,N-dipropyl-paraphenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine and 2-β-hydroxyethylamino-5-aminotoluene, and the acid addition salts thereof.

The para-phenylenediamines may be chosen, for example, from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

The bis(phenyl)alkylenediamines may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4'aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

The para-aminophenols may be chosen, for example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

The ortho-aminophenols may be chosen, for example, from 2-aminophenol, 2-amino-5-methylphenol, 2-amino-6-methylphenol and 5-acetamido-2-aminophenol, and the acid addition salts thereof.

The heterocyclic bases may be chosen, for example, from pyridine derivatives, pyrimidine derivatives and pyrazole derivatives.

The pyridine derivatives may be chosen, for example, from compounds described in patents GB 1 026 978 and GB 1 153 196, such as 2,5-diaminopyridine, 2-(4-methoxyphenyl)amino-3-aminopyridine and 3,4-diaminopyridine, and the acid addition salts thereof.

The pyrimidine derivatives may be chosen, for example, from compounds described in patents DE 2 359 399; JP 88-169 571; JP 05 163 124; and EP 0 770 375 and patent application WO 96/15765, such as 2-hydroxy-4,5,6-triaminopyrimidine, 2,4-dihydroxy-5,6-diaminopyrimidine and pyrazolopyrimidine derivatives, for example, those mentioned in patent application FR-A-2 750 048, such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo-[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and 3-amino-5-methyl-7-imidazolylpropylaminopyrazolo[1,5-a]pyrimidine, the acid addition salts thereof and the tautomeric forms thereof, when a tautomeric equilibrium exists.

The pyrazole derivatives may be chosen, for example, from compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

In another embodiment, the composition may comprise at least one coupler chosen from couplers that are conventionally used in dyeing keratin fibres. Among these couplers, mention may be made, for example, of meta-phenylenediamines, meta-aminophenols, meta-diphenols, naphthalene-based couplers and heterocyclic couplers, and the addition salts thereof.

The at least one coupler may be chosen, for example, from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In another embodiment, the at least one oxidation base and the at least one coupler may be present, for example, in an amount ranging from about 0.001% to about 10% by weight, such as from about 0.005% to about 6% by weight, relative to the total weight of the dye composition.

The acid addition salts of the at least one oxidation base and of the at least one coupler that may be used in the context of the dye composition disclosed herein may be chosen, for example, from hydrochlorides, hydrobromides, sulphates, citrates, succinates, tartrates, lactates, tosylates, benzenesulphonates, phosphates and acetates.

The base addition salts that may be used in the context of the dye composition disclosed herein may be chosen, for example, from the addition salts with sodium hydroxide, potassium hydroxide, ammonia, amines and alkanolamines.

The dye composition may also comprise at least one direct dye. The at least one direct dye may be chosen, for example, from nitrobenzene dyes, cationic direct dyes and azo, methine and azomethine direct dyes.

The medium that is suitable for dyeing, also known as the dye support, generally consists of water or a mixture of water and at least one organic solvent to dissolve compounds that would not be sufficiently soluble in water. The at least one organic solvent may be chosen, for example, from $C_1$–$C_4$ lower alkanols, such as ethanol and isopropanol; polyols and polyol ethers, such as 2-butoxyethanol, propylene glycol, propylene glycol monomethyl ether, diethylene glycol monomethyl ether and monoethyl ether, and aromatic alcohols, such as benzyl alcohol and phenoxyethanol, and mixtures thereof.

The at least one organic solvent may be, for example, in an amount ranging from about 1% to about 40% by weight, further, for example, from about 5% to about 30% by weight, relative to the total weight of the dye composition.

The dye composition may also comprise at least one adjuvant chosen from various adjuvants conventionally used in compositions for dyeing the hair. The at least one adjuvant may be chosen, for example, from anionic, cationic, nonionic, amphoteric and zwitterionic surfactants and mixtures thereof, anionic, cationic, nonionic, amphoteric and zwitterionic polymers and mixtures thereof, mineral and organic thickeners, such as anionic, cationic, nonionic and amphoteric polymeric associative thickeners, antioxidants, penetrating agents, sequestering agents, fragrances, buffers, dispersants, conditioning agents, such as volatile and non-volatile, modified and unmodified silicones, film-forming agents, ceramides, preserving agents and opacifiers.

The at least one adjuvant may be, for example, in an amount ranging from about 0.01% to about 20% by weight relative to the weight of the composition.

Needless to say, a person of ordinary skill in the art may select at least one optional additional compound such that at least one of the advantageous properties intrinsically associated with the oxidation dye composition disclosed herein is not, or is not substantially, adversely affected by the envisaged addition.

The pH of the dye composition may range, for example, from about 3 to about 12, such as from about 5 to about 11. The pH may be adjusted to the desired value, for example, by means of at least one acidifying agent or at least one basifying agent. The at least one acidifying agent or at least one basifying agent may be chosen, for example, from acidifying agents and basifying agents that are usually used in the dyeing of keratin fibres. The pH may also be adjusted, for example, using a standard buffer system.

The acidifying agents may be chosen, for example, from mineral and organic acids, such as hydrochloric acid, orthophosphoric acid, sulphuric acid, carboxylic acids, such as acetic acid, tartaric acid, citric acid and lactic acid, and sulphonic acids.

The basifying agents may be chosen, for example, from aqueous ammonia, alkali metal carbonates, alkanolamines such as monoethanolamine, diethanolamine and triethanolamine and derivatives thereof, sodium hydroxide, potassium hydroxide and the compounds of formula (IV) below:

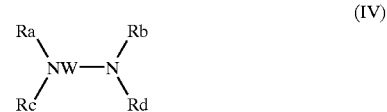

(IV)

wherein W is chosen from propylene residues optionally substituted with at least one radical chosen from hydroxyl and $C_1$–$C_4$ alkyl radicals; Ra, Rb, Rc and Rd, which may be identical or different, are chosen from a hydrogen atom, $C_1$–$C_4$ alkyl radicals and $C_1$–$C_4$ hydroxyalkyl radicals.

The dye composition may be in various forms, such as liquids, creams or gels, or any other form that is suitable for dyeing keratin fibres, such as human hair.

Further disclosed herein is a process for dyeing keratin fibres, such as human keratin fibres, for example, the hair, comprising applying the dyeing composition to the fibres, and the colour can be revealed with atmospheric oxygen or using at least one oxidizing agent.

The colour may be revealed, for example, at acidic, neutral or alkaline pH and the at least one oxidizing agent may be added, for example, to the dyeing composition at the time of use. An oxidizing composition comprising the at least one oxidizing agent may also be used to be applied simultaneously with or sequentially to the dyeing composition.

In one embodiment, the dyeing composition is mixed, for example, at the time of use, with a composition comprising, in a medium that is suitable for dyeing, at least one oxidizing agent, the at least one oxidizing agent being present in an amount sufficient to develop a coloration. The mixture obtained is then applied to the keratin fibres. After leaving the mixture to act for a period of time ranging from about 3 to about 50 minutes, such as from about 5 to about 30 minutes, the keratin fibres are optionally rinsed, washed with shampoo, rinsed again and then dried. In another embodiment, the at least one oxidizing agent is applied to the fibres in the form of an oxidizing composition simultaneously with or sequentially to the dyeing composition.

The at least one oxidizing agent may be chosen, for example, from oxidizing agents used for the oxidation dyeing of keratin fibres, such as hydrogen peroxide, urea peroxide, alkali metal bromates, persalts such as perborates and persulphates, peracids and oxidase enzymes, such as peroxidases, 2-electron oxidoreductases such as uricases and 4-electron oxygenases, for example, laccases. In one embodiment, the at least one oxidizing agent is hydrogen peroxide.

The oxidizing composition may also comprise at least one adjuvant chosen from adjuvants conventionally used in compositions for dyeing the hair. The at least one adjuvant may be chosen, for example, from the adjuvants described above.

The pH of the oxidizing composition comprising the at least one oxidizing agent is such that, after mixing with the dye composition, the pH of the resulting composition applied to the keratin fibres may range, for example, from about 3 to about 12, such as from about 5 to about 11. The pH may be adjusted to the desired value using at least one acidifying agent or at least one basifying agent chosen from acidifying agents and basifying agents usually used in the dyeing of keratin fibres. The at least one acidifying agent or at least one basifying agent may be chosen from acidifying agents and basifying agents described above.

The composition applied to the keratin fibres may be in various forms, such as liquids, creams or gels, or any other form that is suitable for dying keratin fibres, such as human hair.

Further disclosed herein is a multi-compartment device or a multi-compartment dyeing "kit", comprising a first compartment of which comprises the dye composition and a second compartment of which comprises the oxidizing composition. This device may comprise, for example, an implement for applying the mixture to the keratin fibres, such as the devices described in French Patent No. FR-2 586 913.

Illustrative, non-limiting examples are described as follows.

EXAMPLES

Preparation of the Extract of *Myrsine africana*

The extract used is a crude and/or fractionated aqueous extract of the aerial parts of *Myrsine africana*. The expression "aerial parts" means the parts of the plant that are above the soil, i.e., the stems and the leaves. The plant was not in flower during the preparation of this extract.

The leaves and stems were combined, dried at 45° C., ground in a knife mill and then screened through a screen with a mesh size equal to 0.5 μm.

The powder thus obtained was extracted by stirring in the presence of carbonated water at pH 9.5 prepared as follows: anhydrous sodium carbonate was added in a proportion of 1 g/l to distilled water, the pH was adjusted to 9.5 by addition of 1N HCl.

The extraction was performed at room temperature, at a rate of 5 g of plant powder per 100 ml of carbonated water, stirred for 1 hour 30 minutes at 900 rpm.

The mixture was then filtered under vacuum on a filter of porosity 2.7 μm. The filtrate obtained was subsequently frozen and then freeze-dried.

Preparation of the Dye Compositions

1. Coloration in Solution 1.1—Compounds chosen from compounds (IA) and (IB) which are described below were dissolved in a buffer at pH 9.5 to a concentration of 1%. The extract of *Myrsine africana* prepared according to the above procedure was dissolved in water to a concentration of 1%. Compounds (1A) and (1B) are of the following formula:

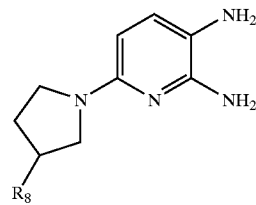

wherein in compounds (IA), R$_8$=H; and in compounds (IB), R$_8$=OH

3% aqueous hydrogen peroxide solution was added to a mixture of these two solutions in a 1/1 weight ratio.

After 10 minutes at room temperature, the appearance of a purple-red coloration was observed.

By performing the same experiment in the absence of *Myrsine africana*, a green coloration is obtained.

The same operation was performed after dissolving compounds chosen from compounds (IA) and (IB) described above in a pH 7 buffer solution; the coloration obtained was then green-blue. By performing the same experiment in the absence of *Myrsine africana*, a green coloration was obtained.

Examples were performed using solutions of compounds chosen from compounds (IA) and (IB) described above at pH 7 and pH 9.5 and of a solution of extract of *Myrsine africana* prepared according to the above procedure but without addition of aqueous hydrogen peroxide solution. The same colorations are observed by oxidation with atmospheric oxygen.

1.2—An example was performed according to the above procedure starting with a composition comprising an extract of *Myrsine africana* and

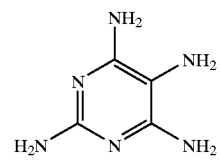

At pH 9.5, an orange coloration was obtained, and at pH 7, a pink coloration was obtained. In the absence of *Myrsine africana*, the coloration was yellow.

1.3—An example was performed according to the above procedure, starting with a composition comprising an extract of *Myrsine africana* and

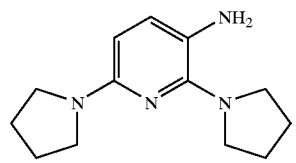

At pH 9.5, a purple-red coloration was obtained, and at pH 7, a green-blue coloration was obtained.

2. Coloration of Keratin Fibres

The above experiments were performed by placing the solution resulting from mixing the solution of dye precursors and of extract of *Myrsine africana* in contact with goat hairs according to the following procedure.

The goat hairs were placed in contact with 1 ml of aqueous extract of *Myrsine africana* at a concentration of 1%, and 1 ml of the solution of compounds chosen from compounds (IA) and (IB) at a concentration of 1% in pH 9.5 buffer was then added. After 20 minutes, the goat hairs were removed from the mixture, rinsed with water and dried at room temperature. They appear dyed a purple-red colour. The same experiment was performed in the presence of aqueous hydrogen peroxide solution. The same purple-red coloration was thus obtained.

The same reaction was performed at pH 7 and allows the goat hair to be dyed a green-blue colour.

What is claimed is:

1. A composition for dyeing keratin fibres by oxidation dyeing comprising, in a medium suitable for dyeing the keratin fibres, at least one extract of *Myrsine africana* and at least one compound chosen from compounds of formula (I) and cosmetically acceptable acid and base addition salts thereof:

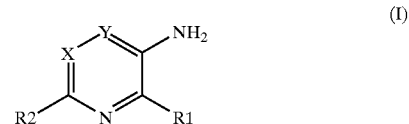

wherein:
R₁ is chosen from radicals of $NR_4R_5$, wherein $R_4$ and $R_5$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_4$ and $R_5$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals; the heterocycle optionally comprising at least one additional hetero atom chosen from O, S, $SO_2$ and NR", wherein R" is chosen from a hydrogen atom and $C_1$–$C_4$ alkyl radicals; $R_2$ is chosen from radicals of $NR_6R_7$, wherein $R_6$ and $R_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_6$ and $R_7$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, the heterocycle optionally comprising at least one additional hetero atom chosen from O, S, $SO_2$ and NR", wherein R" is chosen from a hydrogen atom and $C_1$–$C_4$ alkyl radicals; and X—Y is chosen from RC—CR' and N—CR, wherein R and R', which may be identical or different, are chosen from a hydrogen atom, alkyl, hydroxyl, and amino radicals.

2. The composition according to claim 1, wherein the $C_1$–$C_6$ alkyl radicals are optionally substituted with at least one radical chosen from $C_1$–$C_2$ monoalkylamino and dialkylamino radicals.

3. The composition according to claim 1, wherein the at least one compound chosen from compounds of formula (I) is chosen from compounds of the following formula (Ia):

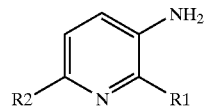

(Ia)

wherein:
R₁ is chosen from radicals of $NR_4R_5$, wherein $R_4$ and $R_5$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_4$ and $R_5$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals; the heterocycle optionally comprising at least one additional hetero atom chosen from O, S, $SO_2$ and NR", wherein R" is chosen from a hydrogen atom and $C_1$–$C_4$ alkyl radicals; and $R_2$ is chosen from radicals of $NR_6R_7$, wherein $R_6$ and $R_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_6$ and $R_7$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, the heterocycle optionally comprising at least one additional hetero atom chosen from O, S, $SO_2$ and NR", wherein R" is chosen from a hydrogen atom and $C_1$–$C_4$ alkyl radicals.

4. The composition according to claim 3, wherein the $C_1$–$C_6$ alkyl radicals are optionally substituted with at least one radical chosen from $C_1$–$C_2$ monoalkylamino and dialkylamino radicals.

5. The composition according to claim 3, wherein $R_1$ is chosen from radicals of $NR_4R_5$, wherein $R_4$ and $R_5$, which may be identical or different, are chosen from a hydrogen atom, alkyl and hydroxyalkyl radicals, or $R_4$ and $R_5$, together with the nitrogen atom to which they are attached, form a 5- to 7-membered ring, and $R_2$ is chosen from radicals of $NR_6R_7$, wherein $R_6$ and $R_7$, which may be identical or different, are chosen from a hydrogen atom, alkyl and hydroxyalkyl radicals, or $R_6$ and $R_7$, together with the nitrogen atom to which they are attached, form a 5- to 7-membered ring.

6. The composition according to claim 3, wherein $R_4$ and $R_5$ are each a hydrogen atom or, together with the nitrogen atom to which they are attached, form a pyrrolidine ring.

7. The composition according to claim 3, wherein $R_6$ and $R_7$, together with the nitrogen atom to which they are attached, form a 1-pyrrolidinyl ring, which is optionally substituted.

8. The composition according to claim 1, wherein the at least one compound chosen from compounds of formula (I) is chosen from compounds of the following formulae (Ia1) and (Ia2):

(Ia1)

(Ia2)

wherein R$_8$ is chosen from a hydrogen atom, halogen atoms, hydroxyl, alkoxy, carboxyl, amino, carboxamido, sulphonamido, monoalkylamino and dialkylamino radicals and C$_1$–C$_6$ alkyl radicals optionally substituted with at least one radical chosen from hydroxyl, amino, carboxyl, monoalkylamino and dialkylamino radicals.

9. The composition according to claim 8, wherein the C$_1$–C$_6$ alkyl radicals optionally substituted with at least one radical chosen from C$_1$–C$_2$ monoalkylamino and dialkylamino radicals.

10. The composition according to claim 1, wherein the at least one compound chosen from compounds of formula (I) is chosen from compounds of the following formula (Ib):

(Ib)

wherein:
R$_1$ is chosen from radicals of NR$_4$R$_5$, wherein R$_4$ and R$_5$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or R$_4$ and R$_5$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and C$_1$–C$_6$ alkyl radicals optionally substituted with at least one radical chosen from hydroxyl, amino, carboxyl, monoalkylamino and dialkylamino radicals; the heterocycle optionally comprising at least one additional hetero atom chosen from O, S, SO$_2$ and NR", wherein R" is chosen from a hydrogen atom and C$_1$–C$_4$ alkyl radicals; R$_2$ is chosen from radicals of NR$_6$R$_7$, wherein R$_6$ and R$_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or R$_6$ and R$_7$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and C$_1$–C$_6$ alkyl radicals optionally substituted with at least one radical chosen from hydroxyl, amino, carboxyl, monoalkylamino and dialkylamino radicals, the heterocycle optionally comprising at least one additional hetero atom chosen from O, S, SO$_2$ and NR", wherein R" is chosen from a hydrogen atom and C$_1$–C$_4$ alkyl radicals; and R is chosen from a hydrogen atom, and alkyl, hydroxyl, and amino radicals.

11. The composition according to claim 10, wherein the C$_1$–C$_6$ alkyl radicals optionally substituted with at least one radical chosen from C$_1$–C$_2$ monoalkylamino and dialkylamino radicals.

12. The composition according to claim 10, wherein R is chosen from amino and hydroxyl radicals.

13. The composition according to claim 12, wherein R, R$_1$ and R$_2$ are each NH$_2$.

14. The composition according to claim 1, wherein said at least one extract of *Myrsine Africana* is a compound of formula (II) below:

(II)

15. The composition according to claim 1, wherein the at least one extract of *Myrsine africana* is in an amount ranging from about 0.1% to about 10% by weight relative to the total weight of the composition.

16. The composition according to claim 1, further comprising at least one oxidation base chosen from para-phenylenediamines, bis(phenyl)alkylenediamines, para-aminophenols, ortho-aminophenols and heterocyclic bases, and addition salts thereof.

17. The composition according to claim 1, further comprising at least one coupler chosen from meta-phenylenediamines, meta-aminophenols, meta-diphenols, naphthalene-based couplers and heterocyclic couplers, and addition salts thereof.

18. The composition according to claim 1, further comprising at least one direct dye.

19. A composition for the oxidation dyeing of keratin fibres comprising, in a medium suitable for dyeing keratin fibres, at least one dye precursor chosen from compounds of formula (I):

(I)

wherein:
R$_1$ is chosen from radicals of NR$_4$R$_5$, wherein R$_4$ and R$_5$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_4$ and $R_5$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals; the heterocycle optionally comprising at least one additional hetero atom chosen from O, S, $SO_2$ and NR", wherein R" is chosen from a hydrogen atom and $C_1$–$C_4$ alkyl radicals; $R_2$ is chosen from radicals of $NR_6R_7$, wherein $R_6$ and $R_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_6$ and $R_7$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, the heterocycle optionally comprising at least one additional hetero atom chosen from O, S, $SO_2$ and NR", wherein R" is chosen from a hydrogen atom and $C_1$–$C_4$ alkyl radicals; and X—Y is chosen from RC—CR' and N—CR, wherein R and R', which may be identical or different, are chosen from a hydrogen atom, alkyl, hydroxyl, and amino radicals; and 3-(β-D-glucopyranosyloxy)-4,5-dihydroxytoluene.

20. The composition according to claim 19, wherein the 3-(β-D-glucopyranosyloxy)-4,5-dihydroxytoluene is obtained from an aqueous extract of *Myrsine africana*.

21. A process for oxidation dyeing of keratin fibres comprising applying to the keratin fibres at least one dyeing composition for a colour to be revealed in the presence of atmospheric oxygen or at least one oxidizing agent, wherein the dyeing composition comprises at least one extract of *Myrsine africana* and at least one compound chosen from compounds of formula (I) and cosmetically acceptable acid and base addition salts thereof:

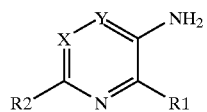

(I)

wherein:

$R_1$ is chosen from radicals of $NR_4R_5$, wherein $R_4$ and $R_5$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_4$ and $R_5$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals; the heterocycle optionally comprising at least one additional hetero atom chosen from O, S, $SO_2$ and NR", wherein R" is chosen from a hydrogen atom and $C_1$–$C_4$ alkyl radicals;

$R_2$ is chosen from radicals of $NR_6R_7$, wherein $R_6$ and $R_7$, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or $R_6$ and $R_7$ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and $C_1$–$C_6$ alkyl radicals optionally substituted with at least one radical chosen from hydroxyl, amino, carboxyl, monoalkylamino and dialkylamino radicals, the heterocycle optionally comprising at least one additional hetero atom chosen from O, S, $SO_2$ and NR", wherein R" is chosen from a hydrogen atom and $C_1$–$C_4$ alkyl radicals; and X—Y is chosen from RC—CR' and N—CR, wherein R and R', which may be identical or different, are chosen from a hydrogen atom, alkyl, hydroxyl, and amino radicals.

22. The process according to claim 21, wherein the keratin fibres are human keratin fibres.

23. The process according to claim 22, wherein the human keratin fibres are hair.

24. The process according to claim 21, wherein the at least one oxidizing agent is chosen from hydrogen peroxide, urea peroxide, alkali metal bromates, persalts, peracids and oxidase enzymes.

25. The process according to claim 21, wherein the at least one oxidizing agent is mixed with the dyeing composition at the time of use.

26. The process according to claims 21, wherein the at least one oxidizing agent is applied to the keratin fibres in a form of an oxidizing composition simultaneously with or sequentially to the dyeing composition.

27. A multi-compartment device or multi-compartment dyeing kit comprising a first compartment comprising a dyeing composition and a second compartment comprising an oxidizing composition, wherein the dyeing composition comprises at least one extract of *Myrsine africana* and at least one compound chosen from compounds of formula (I) and cosmetically acceptable acid and base addition salts thereof:

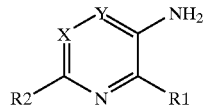

(I)

wherein:

R₁ is chosen from radicals of NR₄R₅, wherein R₄ and R₅, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or R₄ and R₅ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and C₁–C₆ alkyl radicals optionally substituted with at least one radical chosen from hydroxyl, amino, carboxyl, monoalkylamino and dialkylamino radicals; the heterocycle optionally comprising at least one additional hetero atom chosen from O, S, SO₂ and NR", wherein R" is chosen from a hydrogen atom and C₁–C₄ alkyl radicals; R₂ is chosen from radicals of NR₆R₇, wherein R₆ and R₇, which may be identical or different, are chosen from a hydrogen atom and alkyl radicals optionally substituted with at least one radical chosen from hydroxyl, alkoxy, carboxyl, amino, monoalkylamino and dialkylamino radicals in which the alkyl radical is optionally substituted with at least one radical chosen from hydroxyl, alkoxy, carboxyl, amino, monoalkylamino and dialkylamino radicals; or R₆ and R₇ form, together with the nitrogen atom to which they are attached, a 5- to 8-membered saturated heterocycle, the heterocycle possibly being substituted with at least one entity chosen from halogen atoms, hydroxyl, alkoxy, carboxyl, amino, carboxamido, sulphonamido, monoalkylamino and dialkylamino radicals, and C₁–C₆ alkyl radicals optionally substituted with at least one radical chosen from hydroxyl, amino, carboxyl, monoalkylamino and dialkylamino radicals, the heterocycle optionally comprising at least one additional hetero atom chosen from O, S, SO₂ and NR", wherein R" is chosen from a hydrogen atom and C₁–C₄ alkyl radicals; and X—Y is chosen from RC—CR' and N—CR, wherein R and R', which may be identical or different, are chosen from a hydrogen atom, alkyl, hydroxyl, and amino radicals.

\* \* \* \* \*